United States Patent [19]

Chang, deceased

[11] Patent Number: 4,982,029
[45] Date of Patent: Jan. 1, 1991

[54] METHOD FOR THE DIRECT PREPARATION OF OLEFINS FROM KETONES AND GRIGNARD REAGENTS

[75] Inventor: Kuo-Yuan Chang, deceased, late of Midland, Mich., by Richard G. Waterman, legal representative

[73] Assignee: The Dow Chemical Company, Midland, Mich.

[21] Appl. No.: 285,551

[22] Filed: Dec. 16, 1988

[51] Int. Cl.$^5$ ................................................. C07C 1/20
[52] U.S. Cl. ..................................... 585/319; 585/320; 585/469
[58] Field of Search .......................... 585/469, 319, 320

[56] References Cited

U.S. PATENT DOCUMENTS

| | | |
|---|---|---|
| 2,415,878 | 1/1947 | Hale . |
| 2,422,802 | 1/1947 | Schelling et al. . |
| 3,057,932 | 1/1962 | Hiser . |
| 3,651,121 | 1/1972 | Duke et al. . |
| 3,657,373 | 1/1972 | Peterson . |
| 3,665,047 | 1/1972 | Gislon et al. . |
| 3,674,889 | 1/1972 | Schell et al. . |
| 4,228,313 | 10/1980 | Cardenas et al. ................. 585/469 |
| 4,365,103 | 12/1982 | Chang et al. . |
| 4,912,276 | 3/1990 | Puckette ............................ 585/469 |

OTHER PUBLICATIONS

Chemical Abstracts, vol. 40, 544–8.
Chemical Abstracts, vol. 43, 3773.
Chemical Abstracts, vol. 82, 111500g.
Chemical Abstracts, vol. 93, 93:238739t.
Boord et al., "The Grignard Reagent in Hydrocarbon Synthetis", 41 *Industrial & Engineering Chemistry*, 609–615 (1949).
Anonymous, pp. 509–511 and 166–169.

*Primary Examiner*—Curtis R. Davis
*Attorney, Agent, or Firm*—Price, Heneveld, Cooper, DeWitt & Litton

[57] ABSTRACT

A method for the direct preparation of olefins from ketones and Grignard reagents without isolation of the intermediate alcohol and in the absence of acidic dehydration catalysts. Ketones are reacted with a Grignard reagent in the presence of a low boiling solvent for the Grignard reagent to form a Grignard reaction mixture. An active hydrogen-containing compound is added to the Grignard reaction mixture to form a reaction mixture comprising an alcohol and Grignard salts. The alcohol is dehydrated in the presence of the Grignard salts and a solvent which has a higher boiling point than solvents typically emloyed during the Grignard condensation. The higher boiling solvent can be an active hydrogen-containing compound such as n-octanol and otherwise can be added at any time, including the initial condensation step.

31 Claims, No Drawings

METHOD FOR THE DIRECT PREPARATION OF OLEFINS FROM KETONES AND GRIGNARD REAGENTS

BACKGROUND OF THE INVENTION

This invention relates to a process for the preparation of olefins, particularly aryl diolefins. The process is particularly useful for the preparation of diolefinic polymerization initiators such as m-bis-(1-phenylethenyl)-benzene.

A variety of methods are known for preparing unsaturated compounds having one or more carbon-carbon double bonds. Both aliphatic and aromatic olefins and diolefins are prepared commercially by pyrolysis of saturated hydrocarbons. Other methods include reacting an unsaturated alcohol and a ketone or an aldehyde in the presence of carbon monoxide and a catalyst comprising a hydrohalo salt of a Group VIII metal and a germanium or tin salt, and disproportionation and dehydrogenation of more saturated compounds.

Another preparation involves reacting isophthaloyl chloride with benzene. One problem with this approach involves the hazards of handling benzene.

Some of the best methods for preparing aliphatic and aromatic olefins and diolefins involve the dehydration of alcohols. An aromatic diolefin can be prepared by reducing an acylated alkyl halide-substituted aromatic compound to the corresponding aromatic alcohol, dehydrating the alcohol to obtain a vinyl substituted aryl alkyl halide and thereafter subjecting the alkyl halide moiety to dehydrohalogenation conditions to recover the diolefinically-unsaturated aromatic compound. In another process, alcohols are dehydrated and oxydehydrogenated by passing an alcohol-halogen-oxygen mixture over a substantially inert contact-surface such as Alundum and then passing the mixture over a metallic oxide catalyst such as copper chromite to produce dienes such as isoprene.

Among the methods best adapted to the synthesis of aliphatic and aromatic olefins and diolefins in quantity are those which involve the use of the Grignard reaction. In these reactions, an aldehyde, ketone or ester is reacted with a Grignard reagent to form a carbinol. The carbinol is dehydrated to produce an olefin or a mixture of olefins which usually can be separated by fractionation. Typically, in forming olefins and diolefins from alcohol precursors via the Grignard reaction, the alcohols must be separated from their reaction mixture and dehydrated in the presence of acidic catalysts such as paratoluene sulfonic acid, silica gels or aluminum oxides in order to obtain reasonable yields and to inhibit the formation of undesirable by-products. Even when the alcohol is separated from its reaction mixture, the dehydration step will result in formation of undesirable by-products and unacceptable yields unless the dehydration reaction conditions are carefully controlled.

SUMMARY OF THE INVENTION

The present invention is based upon the discovery that an alcohol created by the reaction of a Grignard reagent with an aromatic ketone can be dehydrated, without intermediate separation of the alcohol, in the presence of the magnesium salts resulting from the Grignard condensation and a higher boiling temperature solvent than is normally used in Grignard reactions. The reaction is preferably carried out at temperatures between 130° and 180° C.

DETAILED DESCRIPTION OF THE PREFERRED EMBODIMENT

In the most preferred embodiment, the invention is used to prepare difunctional aromatic olefins, that is, aromatic diolefins, by a process comprising contacting an aromatic diketone with an aliphatic or aromatic Grignard reagent to form a Grignard reaction product; contacting the Grignard reaction product with an active hydrogen-containing compound to form a di-tertiary diol and a Grignard salt; and dehydrating the diol in the presence of the Grignard salt and a high boiling solvent. The dehydration step can be effected without separating the diol from the reaction mixture in which it is formed. The resulting diolefin is exteriorily unsaturated, that is, it contains two pendant $CH_2=C-$ moieties or groups.

The invention comprises a multi-step process in which all process steps can be effected in the same reaction vessel without any intermediate separatory steps. In the first step, an aromatic diketone is reacted with at least a stoichiometric amount of a Grignard reagent to form a Grignard reaction product according to the following reaction scheme:

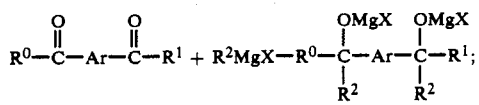

wherein Ar is a divalent substituted or unsubstituted aromatic radical having from 6 to 14 nuclear carbon atoms; $R^0$, $R^1$ and $R^2$ can be the same or different and each is independently methyl or an aromatic group having from 6 to 14 nuclear carbon atoms; with the proviso that, when $R^0$ and $R^1$ are aromatic, $R^2$ must be methyl and when $R^2$ is an aromatic group, $R^0$ and $R^1$ must be methyl; and X is a halogen group, preferably chlorine.

In the second step, the Grignard reaction product is contacted with an active hydrogen-containing compound to form a di-tertiary diol and a Grignard salt according to the following reaction scheme:

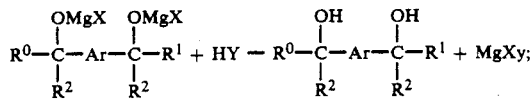

wherein $R^0$, $R^1$, $R^2$, Ar and X are as previously defined and Y is $-OH$, $-OR^3$, halogen or other hydrogen activating substituent; and $R^3$ is an aliphatic group having from 5 to 12 carbon atoms or an aromatic group having from 6 to 14 nuclear carbon atoms.

In the third step, the di-tertiary diol is dehydrated to the aromatic diolefin in the presence of the Grignard salt in a high boiling solvent. "High boiling solvent", at this term is used herein, defines a substantially inert material which has a boiling point greater than solvents used for the Grignard reagent, and preferably in excess of 130° C. The Grignard reagent solvent and reaction solvent must solubolize the Grignard reagent, and this typically means using an ether solvent or equivalent, which in turn typically has a relatively low boiling point, e.g., less than about 130° C.

The dehydration step follows the reaction scheme:

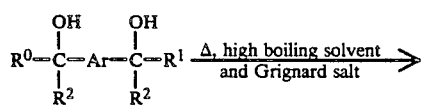

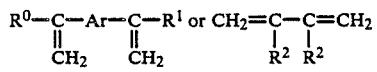

wherein $R^0$, $R^1$ and $R^2$ are as previously described.

The process to form aromatic diolefins having exterior unsaturation can be further illustrated by the following more specific exemplary reactions:

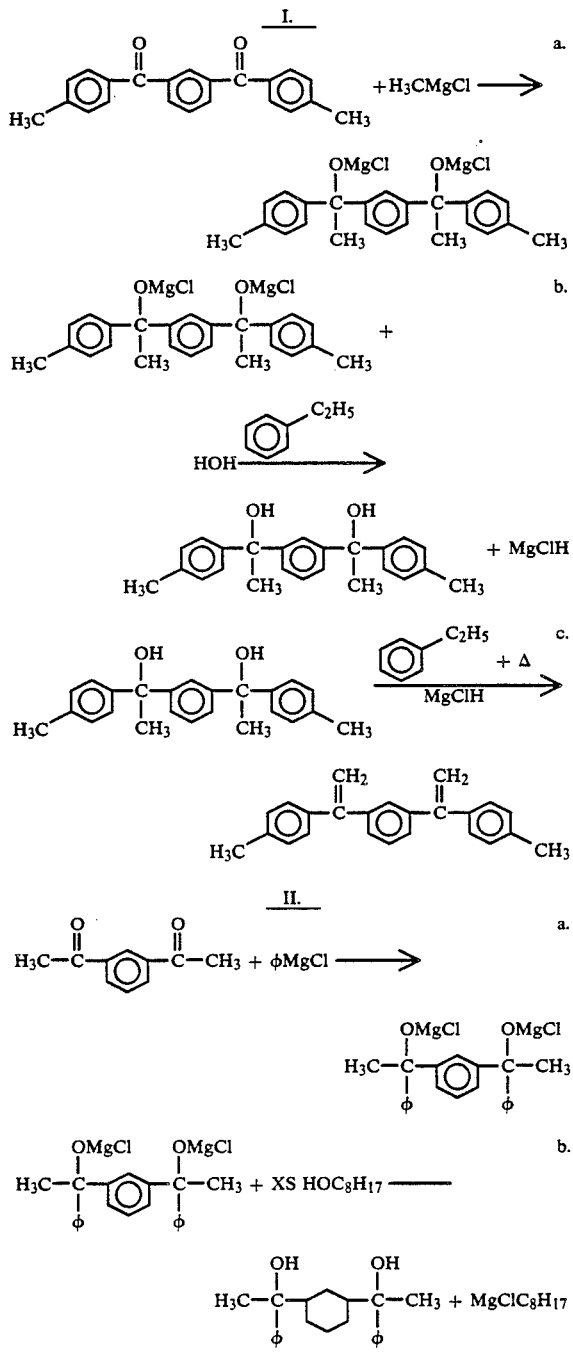

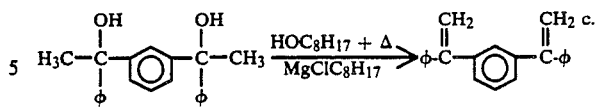

The exemplary reactions I and II illustrate certain important features of the invention. First, in order to make exteriorily unsaturated diolefins, $R^2$ must be methyl when $R^0$ and $R^1$ are other than methyl and, when $R^2$ is other than methyl, $R^0$ and $R^1$ must be methyl. Second, in the alcohol forming step, water can be used as the active hydrogen-containing compound. Third, a high boiling solvent, such as ethyl benzene (b.p. 136.18° C.), which does not itself contain an active hydrogen group, can be present during the alcohol-forming step. The high boiling solvent need not be present during the alcoholysis step, although its presence during this step is currently preferred. Fourth, one can employ a high boiling point solvent which contains an active hydrogen group, such as primary n-octyl alcohol (b.p. 194°–195° C.) or sec-n-octyl alcohol (b.p. 178°–179° C.) in an excess amount during both the alcoholysis and dehydration steps. This latter procedure is currently preferred. Fifth, the entire process can be effected in the same reactor without separating any of the intermediate reaction products. Sixth, the dehydration step is not acid-catalyzed but is promoted by the Grignard salt, which is not separated from the reaction mixture containing the di-tertiary diol. It is a particular feature of the invention that the use of the high boiling point solvent in the presence of the Grignard salt enables the diketone to be converted to the diene without removing the diol from its reaction mixture and without the need for employing an acid catalyst to effect dehydration of the diol.

Substantially any aromatic diketone having the structure:

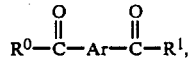

wherein Ar, $R^0$ and $R^1$ are as previously defined, and wherein the points of attachment of the carbonyl groups to the aromatic nucleus are separated from each other by at least one nuclear carbon atom, can be employed in the preferred embodiment of the invention, subject to the caveat previously expressed. Representative aromatic diketones include:

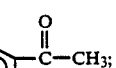

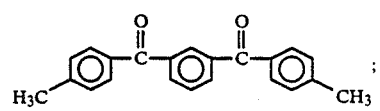

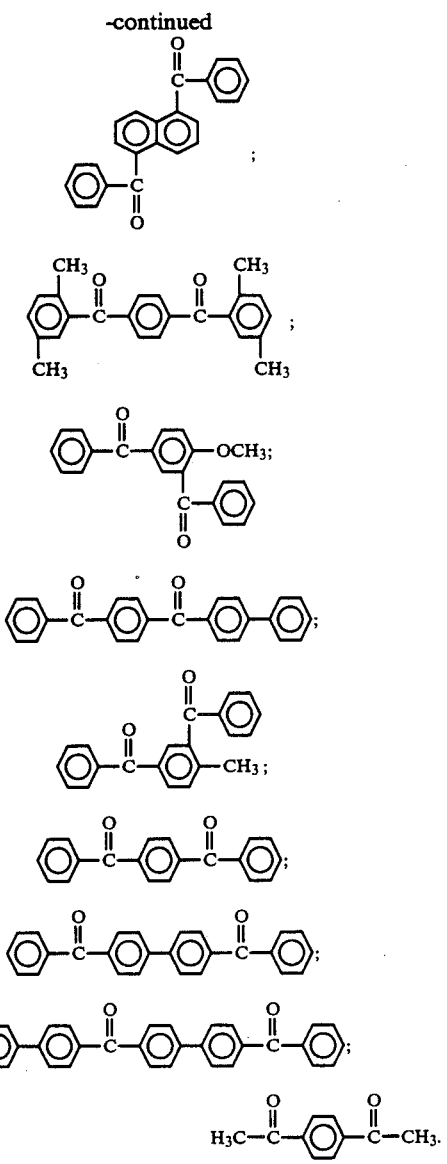

The aromatic diketones are conveniently prepared by reacting aliphatic and aromatic compounds, such as methane, benzene, toluene and biphenyl with an acylating agent such as isophthaloyl chloride in the presence of Friedel-Crafts catalysts.

The Grignard reagents are well-known articles of commerce and need not be discussed in any detail herein. Although substantially any Grignard reagent meeting the substituent requirements outlined above can be employed, methyl magnesium chloride, benzyl magnesium chloride and tolyl magnesium chloride are currently preferred.

The conversion of the Grignard reaction product to the tertiary aromatic diol can be effected by adding a slight excess of a compound containing an active hydrogen, i.e., an easily replaceable hydrogen, such as water, a monoalcohol or a hydrogen halide to the Grignard reaction product mixture whereby the —OMgX moiety is converted to an alcohol and a Grignard salt. While lower alcohols such as ethanol, propanol and t-butanol can be employed for the alcoholysis step, it is preferred to employ monohydric alcohols having a boiling point above 130° C. such as octanol or decanol. Water can also be added to the Grignard reaction mixture for the alcoholysis step, as well as acids such as hydrochloric and sulfuric acids.

The dehydration step is effected in the presence of a solvent having a boiling point which is higher than the solvent which is employed in the Grignard condensation step. The high boiling solvent can be added to the crude reaction mixture which contains both the diol and Grignard salts, without an intermediate separation step to remove the alcohol from the crude reaction mixture. Alternatively, and preferably, the high boiling solvent can be included in the alcoholysis step, either as an active hydrogen-containing compound or in combination with an active hydrogen-containing compound in those cases wherein the high boiling solvent does not itself contain an active hydrogen group. In another variant, high boiling solvents which do not contain any active hydrogen groups, such as ethyl benzene, can be introduced initially, that is, in the first step involving formation of the Grignard reaction product.

It is a particular feature of the process of this invention that the use of the higher boiling solvent in combination with the Grignard salt enables the diketone to be converted to the diene without removing the alcohol from the reaction mixture and without the necessity for employing an acid catalyst to effect the dehydration of the diol. Particularly preferred higher boiling solvents have boiling points above 130° C. and include monoalcohols having at least 5 carbon atoms, preferably 5 to 12 carbon atoms, and aromatic solvents such as ethyl benzene and toluene. Representative high boiling solvents include, without limitation thereto, amyl alcohol, hexyl alcohol, primary n-octanol, sec-n-octanol, isooctanol, decanol, lauryl alcohol, benzene, toluene and ethyl benzene. The use of the higher boiling monoalcohols as a solvent for the dehydration step is particularly beneficial since one can add the alcohol to the Grignard reaction mixture and effect both the alcoholysis step and the dehydration step in the same solvent system. The same end can be accomplished when using aromatic solvents such as ethyl benzene and toluene which do not contain hydrogen-activating substituents by including water with the aromatic solvent when the latter is added to the Grignard reaction mixture.

The reaction of the Grignard reagent with the carbonyl compound is carried out, preferably at atmospheric pressure, in an inert atmosphere such as nitrogen. The reaction is normally conducted in a solvent medium at a temperature from about −60° C. to about 100° C., with room temperature being a preferred reaction temperature. Suitable solvent mediums include saturated hydrocarbons having from 5 to 16 carbon atoms such as pentane, hexane, heptane, octane, isooctane, cyclopentane, cyclohexane and cycloheptane and aromatic hydrocarbons such as benzene, toluene and xylene. Ether solvents such as tetrahydrofuran, dioxane, 1,2-dimethoxyethane, dibutyl ether and diethyl ether are also suitable as solvents in the first step. Ether solvents are preferred, with tetrahydrofuran being particularly preferred when aromatic Grignard reagents are employed. Preferably, the solvent medium will be the same solvent in which the Grignard reagent was prepared or provided, since the preferred solvents for the first step of the synthesis should be one in which the Grignard reagent is soluble.

Performing the dehydration step without separating the diol enables one to use the magnesium salts which are formed during the alcoholysis reaction as a promoter for the dehydrogenation step.

The dehydration step is effected at a temperature in the range from 130° C. to 180° C. with the low boiling ether or alcohol solvent being removed from the reaction vessel by distillation. At temperatures below 130° C., dehydration is unacceptably slow and undesirable reactions leading to by-product formation occur at temperatures higher than 180° C.

The following examples are illustrative of the invention and should not be taken as limiting the scope of the claims.

EXAMPLE 1

Preparation of M-Bis-(1-Phenylethenyl) Benzene

A Grignard reaction mixture was prepared by contacting 100 mL of 2M phenylmagnesium chloride in tetrahydrofuran with 0.1 mole m-diacetyl benzene. 100 mL of n-octanol were added to the Grignard reaction mixture. The tetrahydrofuran was removed by distillation during which the pot temperature rose to 175° C. in 2 hours. Gas chromatograph analysis showed that the alcohol had been dehydrated to m-bis-(1-phenylethenyl) benzene. Product yield was about 95%

EXAMPLE 2

A Grignard reaction was prepared by contacting 100 mL of 2M phenylmagnesium chloride with 0.1 mole N-acetyl benzene in tetrahydrofuran. 3 grams of water and 100 mL of ethyl benzene were added to the Grignard reaction mixture. The tetrahydrofuran was removed by distillation during which the pot temperature rose to 135° C. The reaction mixture was maintained at this temperature for 1 hour.

Gas chromatograph analysis showed that substantially all of the alcohol had been dehydrated to m-bis-(1-phenylethenyl) benzene.

The yield of m-bis-(1-phenylethenyl) benzene was about 95%.

The embodiments of the invention in which an exclusive property or privilege is claimed are defined as follows.

1. A process for preparing an unsaturated compound having two exterior carbon-carbon double bonds comprising:
   contacting an aromatic compound containing two acyl groups with at least one Grignard reagent in an inert solvent medium in which said Grignard reagent is soluble to form a first reaction mixture comprising a Grignard reaction product;
   contacting said first reaction mixture comprising a Grignard reaction product with at least one active hydrogen-containing compound to form a second reaction mixture comprising a compound having two tertiary hydroxyl groups and a Grignard salt; and
   heating said second reaction mixture in the presence of a solvent having a boiling point greater than about 130° C. to a temperature in the range of 130° to 180° C. to dehydrate said compound having two tertiary hydroxyl groups to form an unsaturated compound having two exterior carbon-carbon double bonds.

2. A process according to claim 1 wherein said aromatic compound has at least one aromatic ring.

3. A process according to claim 1 wherein said compound containing two acyl groups comprises m-diacetylbenzene 4. A process according to claim 3 wherein said Grignard reagent comprises phenylmagnesium chloride.

5. A process according to claim 4 wherein said active hydrogen-containing compound comprises n-octanol.

6. A process according to claim 4 wherein said active hydrogen-containing compound comprises water.

7. A process according to claim 6 wherein said solvent having a boiling point greater than about 130° C. comprises n-octanol.

8. A process according to claim 6 wherein said solvent having a boiling point greater than about 130° C. comprises ethyl benzene.

9. A process according to claim 1 wherein said unsaturated compound having two carbon-carbon double bonds comprises m-bis-(phenylethenyl)benzene.

10. A process according to claim 1 wherein said Grignard reagent comprises methyl magnesium chloride.

11. A process according to claim 10 wherein said compound containing two acyl groups comprises m-diacetyl benzene.

12. A process according to claim 10 wherein said compound containing two acyl groups comprises benzoyl benzophenone.

13. A process according to claim 11 wherein said active hydrogen-containing compound comprises water.

14. A process according to claim 11 wherein said active hydrogen-containing compound comprises n-octanol.

15. A process according to claim 13 wherein said solvent having a boiling point greater than about 130° C. comprises ethyl benzene.

16. A process according to claim 12 wherein said active hydrogen-containing compound comprises water.

17. A process according to claim 12 wherein said active hydrogen-containing compound comprises n-octanol.

18. A process according to claim 16 wherein said solvent having a boiling point greater than about 130° C. comprises ethyl benzene.

19. A process according to claim 1 wherein said first reaction mixture is contacted with at least one solvent having a boiling point greater than about 130° C. in the presence of said active hydrogen-containing compound.

20. A process according to claim 19 wherein said active hydrogen-containing compound comprises water and said solvent having a boiling point greater than about 130° C. comprises ethyl benzene.

21. A process according to claim 19 wherein said active hydrogen-containing compound and said solvent having a boiling point greater than about 130° C. are the same.

22. A process according to claim 21 wherein said active hydrogen-containing compound and said solvent having a boiling point greater than about 130° C. comprises n-octanol.

23. A process according to claim 1 wherein said compound containing two acyl groups has the formula

wherein Ar is a divalent substituted or unsubstituted aromatic radical having from 6 to 14 nuclear carbon atoms; $R^0$ and $R^1$ can be the same or different and each is independently methyl or an aromatic group having from 6 to 14 nuclear carbon atoms.

24. A process according to claim 23 wherein said Grignard reagent has the formula $R^2MgX$, wherein $R^2$ is a methyl or an aromatic group having from 6 to 14 nuclear atoms and X is a halogen group, with the proviso that when $R^0$ and $R^1$ are methyl or an aromatic group having from 6 to 14 nuclear carbon atoms, $R^3$ is methyl, and when $R^2$ is an aromatic group having from 6 to 14 nuclear carbon atoms, $R^0$ and $R^1$ are methyl.

25. A process according to claim 23 wherein said $R^1$ and $R^2$ are methyl.

26. A process according to claim 25 wherein said Grignard reagent comprises phenyl magnesium chloride.

27. A process according to claim 25 wherein said Grignard reagent comprises methyl magnesium chloride.

28. A process according to claim 23 wherein $R^1$ and $R^2$ are phenyl.

29. A process according to claim 28 wherein said Grignard reagent comprises methyl magnesium chloride.

30. A process according to claim 23 wherein $R^1$ and $R^2$ are toluene.

31. A process according to claim 30 wherein said Grignard reagent comprises methyl magnesium chloride.

* * * * *